US00PP12732P2

(12) United States Plant Patent
Dupont, Sr.

(10) Patent No.: US PP12,732 P2
(45) Date of Patent: Jun. 25, 2002

(54) HIBISCUS PLANT NAMED 'EVANGELINE'

(75) Inventor: Robert J. Dupont, Sr., Plaquemine, LA (US)

(73) Assignee: DuPont Nursery, Inc., Plaquemine, LA (US)

( * ) Notice: Subject to any disclaimer, the term of this patent is extended or adjusted under 35 U.S.C. 154(b) by 11 days.

(21) Appl. No.: 09/761,475

(22) Filed: Jan. 18, 2001

(51) Int. Cl.[7] ..... A01H 5/00

(52) U.S. Cl. ..... Plt./257

(58) Field of Search ..... Plt./257

*Primary Examiner*—Bruce R. Campell
*Assistant Examiner*—Michelle Kizilkaya
(74) *Attorney, Agent, or Firm*—C. A. Whealy

(57) ABSTRACT

A new and distinct cultivar of Hibiscus plant named 'Evangeline', characterized by its glossy dark green leaves; upright, compact and freely branching plant habit; freely flowering habit; and large pink and yellow-colored flowers with dark red centers.

2 Drawing Sheets

BACKGROUND OF THE INVENTION

The present invention relates to a new and distinct cultivar of Hibiscus, botanically known as *Hibiscus rose-sinensis* and hereinafter referred to by the cultivar name Evangeline.

The new Hibiscus is a product of a planned breeding program conducted by the Inventor in Plaquemine, La. The objective of the breeding program is to create new large-flowered Hibiscus cultivars with unique and desirable flower colors.

The new Hibiscus originated from a cross made by the Inventor in Plaquemine, La., of the *Hibiscus rosa-sinensis* cultivar Topaz Glory, not patented, as the female, or seed, parent with the *Hibiscus rosa-sinensis* cultivar Gina Marie, not patented, as the male, or pollen, parent. The cultivar Evangeline was discovered and selected by the Inventor as a flowering plant within the progeny of the stated cross in a controlled environment in Plaquemine, La.

Compared to plants of the topaz-flowered female parent, the cultivar Topaz Glory, plants of the new Hibiscus are more compact and more freely branching.

Compared to plants of the light pink-flowered male parent, the cultivar Gina Marie, plants of the new Hibiscus are more compact, more freely branching, and more freely flowering.

Asexual reproduction of the new Hibiscus by terminal cuttings taken in a controlled environment in Plaquemine, La., has shown that the unique features of this new Hibiscus are stable and reproduced true to type in successive generations.

SUMMARY OF THE INVENTION

The cultivar Evangeline has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Evangeline'. These characteristics in combination distinguish 'Evangeline' as a new and distinct cultivar:

1. Glossy dark green leaves.
2. Upright, compact and freely branching plant habit that is appropriate for container production.
3. Freely flowering habit.
4. Large pink and yellow-colored flowers with dark red centers.

BRIEF DESCRIPTION OF THE PHOTOGRAPHS

The accompanying colored photographs illustrate the overall appearance of the new Hibiscus, showing the colors as true as it is reasonably possible to obtain in colored reproductions of this type. Colors in the photographs may differ slightly from the color values cited in the detailed botanical description which accurately describe the colors of the new Hibiscus.

The photograph on the first sheet comprises a side perspective view of a typical plant of 'Evangeline' that was about 12 months old.

The photograph on the second sheet comprises a close-up view of a typical flower of 'Evangeline'.

DETAILED BOTANICAL DESCRIPTION

The following observations, measurements and values describe plants grown in Plaquemine, La., with one plant per 12.5-cm container, during the summer under outdoor conditions which closely approximate commercial production. Plants used for the description were about 9 months old. In the description, color references are made to The Royal Horticultural Society Colour Chart except where general terms of ordinary dictionary significance are used.

Botanical classification: *Hibiscus rosa-sinensis* cultivar Evangeline.

Parentage:

*Female or seed parent.*—*Hibiscus rosa-sinensis* cultivar Topaz Glory, not patented.

*Male or pollen parent.*—*Hibiscus rosa-sinensis* cultivar Gina Marie, not patented.

Propagation:

*Type.*—By terminal cuttings.

*Time to initiate roots.*—Summer: About 30 days at temperatures of 22° C. Winter: About 40 days at temperatures of 22° C.

*Time to develop roots.*—Summer: About 60 days at temperatures of 22° C. Winter: About 70 days at temperatures of 22° C.

*Root description.*—Fibrous and well-branched.

Plant description:

*Plant form and growth habit.*—Perennial evergreen; upright and compact plant habit.

*Branching habit.*—Freely branching, usually about four lateral branches develop after removal of terminal apex.

*Plant height, soil level to top of flowers.*—About 25 cm.

*Plant diameter, area of spread.*—About 37 cm.

*Lateral branch description.*—Length: About 17.5 cm. Diameter: About 6.5 mm. Texture: Immature, smooth; mature, woody and rough. Color: Immature: Green, more green than 147A. Mature: Brownish gray, close to 200C with 197A overtones.

Foliage description:

*Arrangement.*—Alternate, single; numerous; symmetrical.

*Length.*—About 9.75 cm.

*Width.*—About 7.6 cm.

*Shape.*—Ovate.

*Apex.*—Acute.

*Base.*—Obtuse.

*Margin.*—Crenate.

*Texture.*—Glabrous; rugose.

*Color.*—Young foliage, upper surface: More green than 147A; very glossy. Young foliage, lower surface: Close to 146A. Mature foliage, upper surface: Much darker than 147A; glossy. Mature foliage, lower surface: Close to 147A.

*Petiole.*—Length: About 3.3 cm. Diameter: About 2.5 mm. Texture: Very fine pubescence on upper surface; lower surface, glabrous. Color: Dark greenish brown; close to 200A with undertones of 147A.

Flower description:

*Natural flowering season.*—Spring through fall or during periods of warm weather.

*Flower arrangement.*—Flowers arranged singly at terminal leaf axils. Very freely flowering with usually about two or three developing flower buds and one or two open flowers per lateral branch. Flowers face mostly upright.

*Flower appearance.*—Large, rounded single flowers. Flowers are open for about one to two days before closing. Flowers persistent.

*Flower diameter.*—About 18.5 cm.

*Flower depth.*—About 8.4 cm.

*Flower bud* (*just before showing color*).—Rate of opening: About three to five days depending on temperatures. Length: About 2.5 cm. Diameter: About 1.2 cm. Shape: Ovoid. Color: More green than 147A.

*Petals.*—Texture: Smooth, satiny, rugose. Arrangement: Corolla consists of five overlapping petals. Shape: Roughly spatulate. Apex: Mostly rounded. Base: Truncate. Margin: Entire; undulate and ruffled. Length: About 9.3 cm. Width: About 9.2 cm. Color: Upper surface: Margin, yellow, 10A to 10B, with faint pink, 54A to 54B, overtones; center, pink, 54A to 54B to 54C, veins, white, 155D; base, dark red, 53A, and shiny. Lower surface: Margin, 10B; center, 10D; base, white, 155D.

*Sepals.*—Appearance: Five sepals fused into a star-shaped calyx. Shape: Elongated oblong. Apex: Acute. Length: About 3.3 cm. Width: About 1.5 cm. Texture: Smooth. Color: Upper surface: Close to 146A. Lower surface: Close to 147A.

*Peduncles.*—Length: About 3.1 cm. Diameter: About 3 mm. Angle: Mostly upright to slightly bent. Strength: Strong, flexible. Texture: Smooth. Color: Slightly darker than 146A.

*Reproductive organs.*—Androecium: Stamen number: Numerous, about 55. Anther shape: Crescent. Anther size: About 2 mm by 1 mm. Anther color: 12A. Amount of pollen: Moderate. Pollen color: 15A. Gynoecium: Pistil number: One. Pistil length: About 7.6 cm. Style length: About 6.1 cm. Style diameter, at base: About 8 mm. Style color: Base, 53A; mid-section, close to 49A; apex, 155D. Stigma number: Five. Stigma shape: Rounded. Stigma diameter: About 2 mm. Stigma color: 15A to 17A.

*Seed.*—Seed production has not been observed.

Disease resistance: Plants of the new Hibiscus have not been observed to be resistant to pathogens common to Hibiscus.

It is claimed:

1. A new and distinct Hibiscus plant named 'Evangeline', as illustrated and described.

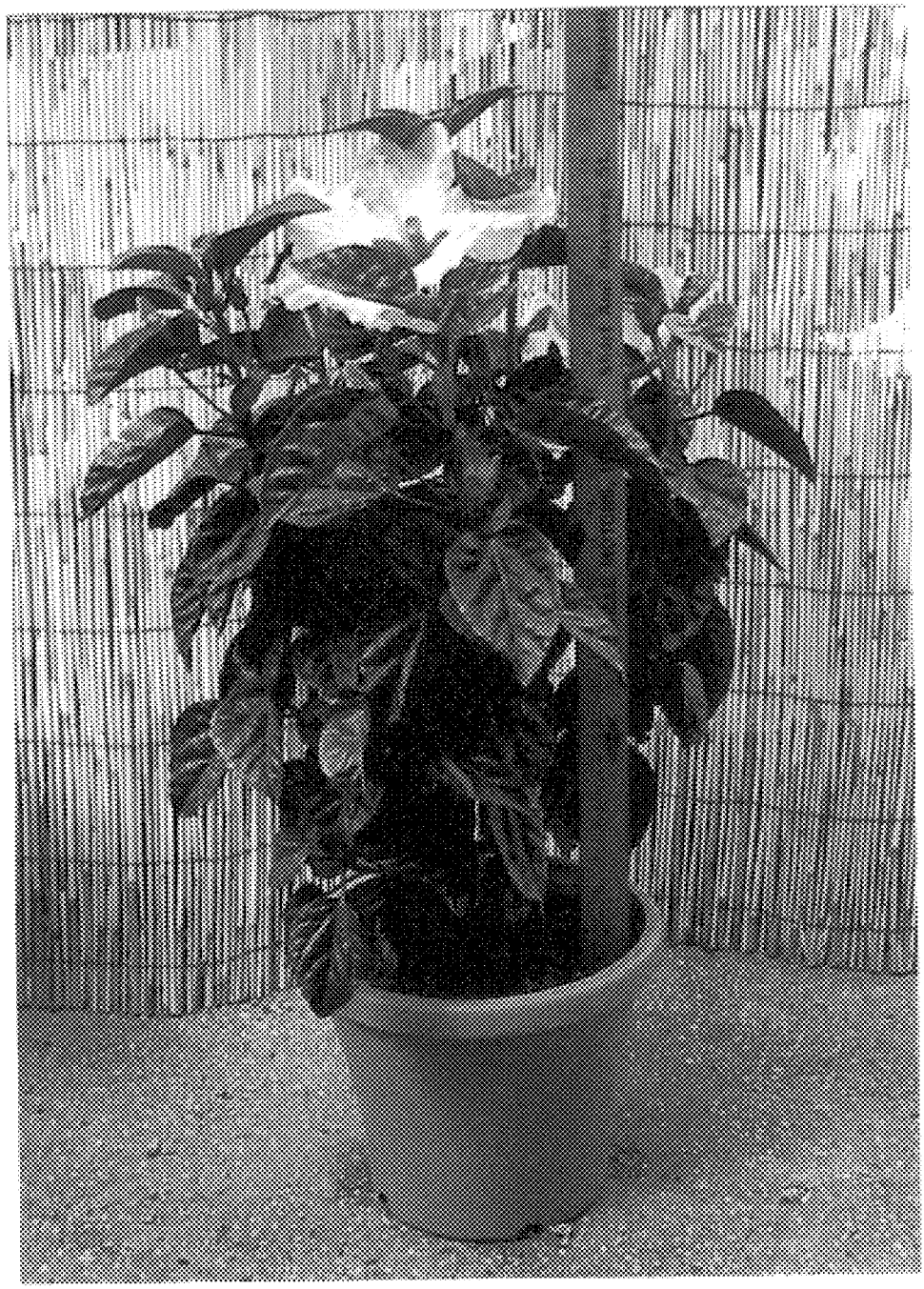

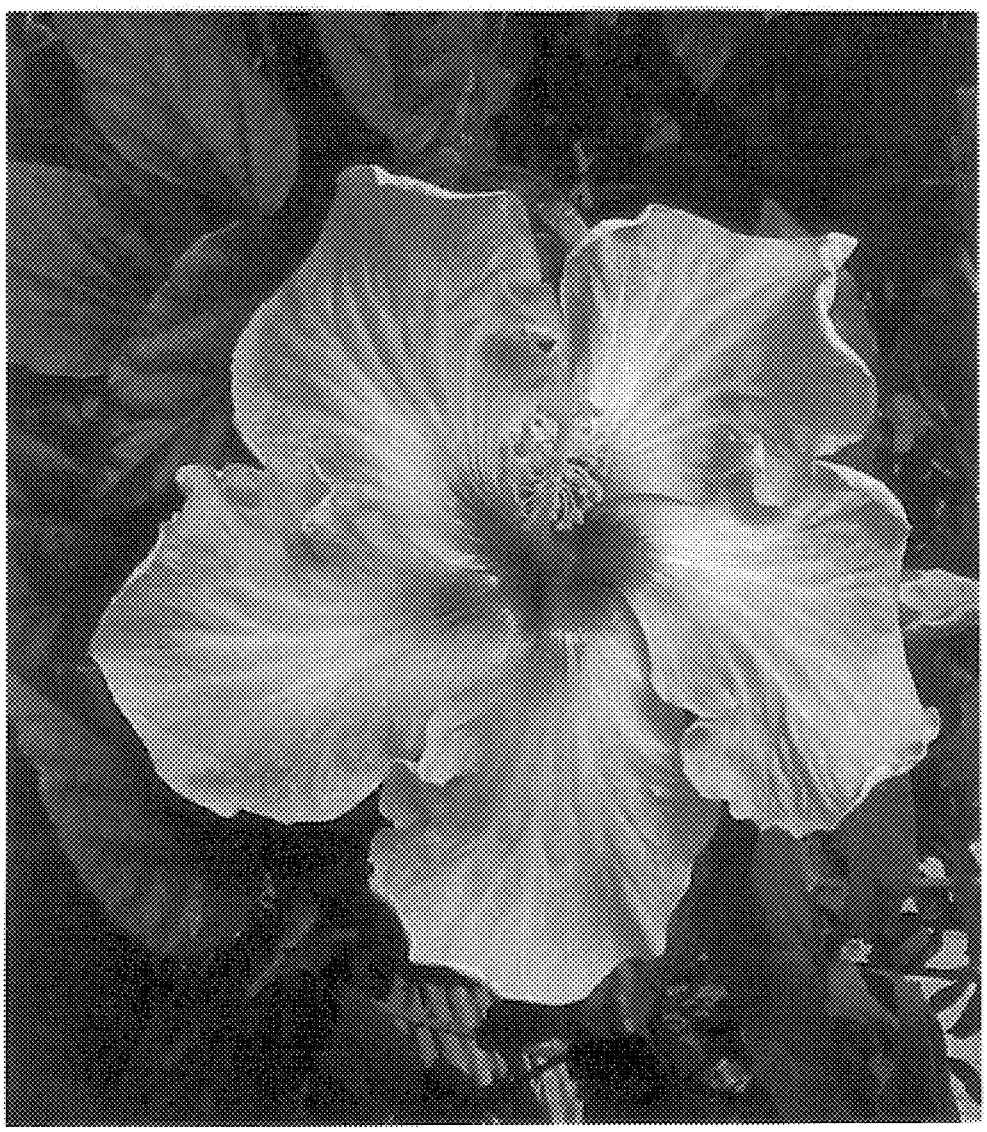

* * * * *